United States Patent [19]

Sagiv et al.

[11] Patent Number: 5,552,875
[45] Date of Patent: Sep. 3, 1996

[54] METHOD AND APPARATUS FOR FORMING DUPLEX IMAGES ON A SUBSTRATE

[75] Inventors: Oded Sagiv, Cochav Yair, Israel; Benzion Landa, Edmonton, Canada; Yoram Blum, Givat Shmuel, Israel

[73] Assignee: Indigo N.V., Veldhoven, Netherlands

[21] Appl. No.: 185,812

[22] PCT Filed: Aug. 14, 1991

[86] PCT No.: PCT/NL91/00151

§ 371 Date: Sep. 8, 1994

§ 102(e) Date: Sep. 8, 1994

[87] PCT Pub. No.: WO93/04409

PCT Pub. Date: Mar. 4, 1993

[51] Int. Cl.$^6$ ..................................................... G03G 21/00
[52] U.S. Cl. .......................... 355/319; 271/3.03; 271/184; 271/301; 355/315
[58] Field of Search ...................... 355/315, 319; 271/184, 301, 302, 303, 307, 311, 3.03

[56] References Cited

U.S. PATENT DOCUMENTS

| | | | |
|---|---|---|---|
| 3,987,756 | 10/1976 | Katayama et al. | 355/327 X |
| 4,428,667 | 1/1984 | Phelps et al. | 355/317 |
| 4,568,169 | 2/1986 | Wada et al. | 355/319 |
| 4,639,126 | 1/1987 | Bushaw et al. | 355/320 |
| 4,804,175 | 2/1989 | Grandjean | 271/184 X |
| 4,806,979 | 2/1989 | Tokoro et al. | 355/319 |
| 4,814,822 | 3/1989 | Acquaviva et al. | 355/319 X |
| 4,815,378 | 3/1989 | Stienstra | 271/186 X |
| 4,990,965 | 2/1991 | Kiya | 355/319 |
| 5,040,029 | 8/1991 | Rodenberg et al. | 355/327 X |
| 5,296,908 | 3/1994 | Hatano et al. | 355/319 |

FOREIGN PATENT DOCUMENTS

| | | |
|---|---|---|
| 0147341 | 7/1985 | European Pat. Off. . |
| 0342704 | 11/1989 | European Pat. Off. . |
| 0372294 | 6/1990 | European Pat. Off. . |
| 2099759 | 12/1982 | United Kingdom . |

*Primary Examiner*—Fred L. Braun
*Attorney, Agent, or Firm*—Greenblum & Bernstein P.L.C.

[57] ABSTRACT

Imaging apparatus for duplex printing on a substrate having first and second sides and a leading edge and a trailing edge, the imaging apparatus including a first member having an image support surface adapted to sequentially support first and second images thereon, a second member adapted to support the substrate such that one side of the substrate engages the image support surface, leading edge first, at a transfer region and transfer apparatus for transferring the first image from the image support surface to the first side of the substrate at the transfer region while at least partially fixing the image thereto. The imaging apparatus also includes a waiting station adjacent the second member for receiving the substrate after transfer of the first image thereto and prior to the transfer of the second image thereto and an output station for receiving the substrate after completion of image transfer thereto. The imaging apparatus includes deflector apparatus adjacent the second member operative to receive the substrate directly from the second member and selectably deflect the substrate towards the waiting station or the output station for delivery thereto and roller apparatus associated with the waiting station for selectably engaging the trailing edge of the substrate after the substrate has been delivered to the waiting station for delivering the substrate back to the second member. The second member is operative to deliver the substrate to the transfer region, whereat the second image is transferred to the second side of the substrate.

44 Claims, 6 Drawing Sheets

METHOD AND APPARATUS FOR FORMING DUPLEX IMAGES ON A SUBSTRATE

FIELD OF THE INVENTION

The present invention relates generally to liquid toner electrographic imaging systems and more particularly to duplex printing apparatus for liquid toner electrographic imaging systems.

BACKGROUND OF THE INVENTION

Apparatus for duplex copying of documents and for duplex printing by means of laser printers are known in the art. U.S. Pat. No. 4,949,949 to Holmes et al. describes a "Hybrid Sequencing Duplex Automatic Document Handling System" which includes apparatus for handling document sheets both sides of which are to be copied and for making duplex (i.e. double-sided) copies of such document sheets. The apparatus involve the use of one or more pairs of reversible rollers, lengthy inversion paths, and buffer trays for the handling of the documents and the copy paper prior to and in the course of making duplex copies. U.S. Pat. No. 4,884,794 to Dinatale et al. describes a document handler for duplex photocopying having first and second inverting path segments, which are utilized to re-orient the copy paper prior to duplex copying. U.S. Pat. No. 5,003,355 to Tanzawa describes a sheet transport control apparatus for use in a duplex unit of a laser printer, the apparatus including a transport system and a switchback system, and a series of driving motors and sensors. All the systems described in the prior art share the common feature of being mechanically complex, and they all involve transporting the paper through relatively lengthy and convoluted paths after printing on the first side so as to be able to print on the second side.

SUMMARY OF THE INVENTION

The present invention provides apparatus and a method for duplex printing that is significantly simpler than those described in the prior art. More specifically, the present invention provides apparatus and a method for duplex printing involving a short and straight transport path, without need for inverting segments and/or complex control mechanisms. As a consequence, the present invention affords duplex printing that is remarkably fast and efficient, and enables printing on both sides of a sheet of paper without any significant waiting time. There is therefore provided in accordance with the invention imaging apparatus for duplex printing on a substrate having first and second sides and a leading edge and a trailing edge, the apparatus including:

a first member having an image support surface adapted to sequentially support first and second images thereon;

a second member adapted to support the substrate such that one side of the substrate engages the image support surface, leading edge first, at a transfer region;

means for transferring the first image from the image support surface to the first side of the substrate at the transfer region while at least partially fusing and fixing the image thereon;

a waiting station adjacent the second member for receiving the substrate after transfer of the first image thereto and prior to the transfer of the second image thereto;

an output station for receiving the substrate after completion of image transfer thereto;

deflector means adjacent the second member operative to receive the substrate directly from the second member and selectably deflect the substrate towards the waiting station or the output station for delivery thereto; and roller means associated with the waiting station for selectably engaging the trailing edge of the substrate after the substrate has been delivered to the waiting station and for delivering the substrate back to the second member, the second member being operative to deliver the substrate to the transfer region, whereat the second image is transferred to the second side of the substrate.

In accordance with a preferred embodiment of the invention, the second member includes gripping means for gripping the edge of the substrate which enters the transfer region first and is adapted for repeatedly engaging the same side of the substrate with the image support surface, such that at each engagement a different color image is transferred thereto.

In accordance with another preferred embodiment of the invention, the deflector means includes a roller and a set of wheels engaging the roller and forming a nip through which the substrate is transported, the set of wheels being adapted to engage the roller at first and second positions, at the first position the angle of release of the substrate from the nip is such that it is deflected to the waiting station, and at the second position the angle of release of the substrate from the nip is such that the it is deflected to the output tray.

In accordance with yet another preferred embodiment of the invention, the deflector means includes:

a shaft;

a motorized roller;

pairs of arms joined to each other at a pivot and spring-loaded with respect to each other at the pivot, one of the arms fixedly attached to the shaft and the other arm having a wheel rotatably attached thereto and forming a nip with respect to the roller; and means for rotating the shaft to first and second positions, whereby at the first position the deflector means is operative to deflect the substrate to the waiting station and at the second position the deflector means is operative to deflect the substrate to the output station.

In accordance with another preferred embodiment of the invention, the pairs of arms which are part of the deflector means are axially distanced from each other along the shaft and are axially slideable along the shaft. The shaft also includes stiffener members axially slideable thereon.

In accordance with another preferred embodiment of the invention, the deflector means is operative to deflect a substrate to the waiting station while the roller means is operative to deliver a different substrate from the waiting station back to the second member.

In accordance with yet another preferred embodiment of the invention, the roller means includes a motorized set of wheels and a roller selectably adapted to engage the trailing edge of the substrate at a nip formed with the wheels. In this embodiment, the roller is in an open, disengaged position with respect to the wheels prior to the deflection of a substrate to the waiting station, such that the trailing edge of the substrate contacts the wheels when it is deflected to the waiting station, and the roller is in a closed, engaged position with respect to the wheels when the substrate is delivered back to the second member.

In accordance with another preferred embodiment of the invention, the roller means includes:

a base plate having at least one aperture therethrough;

a motorized rotatable shaft having at least one rubberized wheel mounted thereon and extending through the aperture; and at least one roller pivotally mounted with respect to the plate, and selectably operative to form a nip with respect to the at least one wheel for delivery of a substrate therethrough, whereby the at least one roller is in a first disengaged position with respect to the at least one wheel prior to the deflection of a substrate to the waiting station and in a closed, engaged position with respect to the at least one wheel when the substrate is delivered back to the second member.

In accordance with another preferred embodiment of the invention, the imaging apparatus includes means for causing the engagement of the first sides of sequential substrates with the image bearing surface for image transfer thereto prior to causing the engagement of the second sides of sequential substrates for image transfer thereto.

In accordance with yet another preferred embodiment of the invention, there is provided apparatus for printing toner images on both sides of a plurality of sequential substrates, the apparatus including:

printing means for printing toner images on one side of a substrate;

a waiting station spaced closely to the printing means and adapted for holding only one substrate at any one time after printing of images on the first side thereof; and delivery means associated with the waiting station for delivering a substrate from the waiting station back to the printing means for printing on the second side thereof, a first substrate being removed from the waiting station while another substrate is being delivered to the waiting station after printing on the first side thereof.

In accordance with another preferred embodiment of the invention, there is provided a method for printing images on first and second sides of sequential substrates, the method comprising the steps of:

(a) printing an image on the first side of a first substrate;

(b) delivering the first substrate to a waiting station;

(c) printing an image on the first side of a subsequent substrate;

(d) delivering the subsequent substrate to the waiting station while removing the first substrate therefrom;

(e) printing an image on the second side of the first substrate;

(f) delivering the first substrate to an output station while removing the second substrate from the waiting station;

(g) printing an image on the second side of the subsequent substrate.

(g) repeating steps (a)–(f) above for a plurality of sequential substrates.

In accordance with yet another preferred embodiment of the invention, there is provided a method for printing images on first and second sides of sequential substrates, the method comprising the steps of:

(a) printing an image on the first side of a first substrate;

(b) delivering the first substrate to a waiting station;

(c) printing an image on the first side of a subsequent substrate;

(d) delivering the subsequent substrate to the waiting station while removing the first substrate therefrom;

(e) printing an image on the second side of the first substrate;

(f) delivering the first substrate to an output station;

(g) printing an image on the first side of a third substrate;

(h) delivering the third substrate to the waiting station while removing the second substrate from the waiting station;

(i) printing an image on the second side of the second substrate.

(j) repeating steps (g)–(i) a plurality of times.

There is further provided, in accordance with a preferred embodiment of the invention, a method for printing images on first and second sides of sequential substrates utilizing apparatus having an image bearing roller and an impression roller forming a nip therebetween, including the steps of:

(a) passing a first substrate through the nip during a first revolution of the image bearing roller to print an image on the first side of a first substrate;

(b) delivering the first substrate to a waiting station;

(c) passing a second substrate through the nip during a subsequent revolution of the image bearing roller to print an image on the first side of the second substrate; and (e) passing the first substrate through the nip during the next revolution of the image bearing roller after the subsequent revolution to print an image on the second side of the first substrate.

In a further preferred embodiment of the invention there is provided a method for printing images on first and second sides of sequential substrates utilizing apparatus having an image bearing roller and an impression roller forming a nip therebetween, including the steps of:

(a) passing a first substrate through the nip during a first series of revolutions of the image bearing roller to print a plurality of color separation images on the first side of a first substrate;

(b) delivering the first substrate to a waiting station;

(c) passing a second substrate through the nip during a subsequent revolution of the image bearing roller thereby printing an image on the first side of the second substrate; and (e) passing the first substrate through the nip during the next revolution of the image bearing roller after the subsequent revolution to print an image on the second side of the first substrate.

In a preferred embodiment of the invention the method and includes the step of passing the second substrate through the nip at least one time between step (a) and step (c) thereby to print at least one additional image on the first side of the second substrate.

Preferably, the first and second images are toner images, more preferably liquid toner images.

In a preferred embodiment of the invention different images are printed on the first and second substrates.

BRIEF DESCRIPTION OF THE DRAWINGS

The present invention will be understood and appreciated from the following detailed description, taken in conjunction with the drawings in which.

DETAILED DESCRIPTION OF PREFERRED EMBODIMENTS

Figure 1:
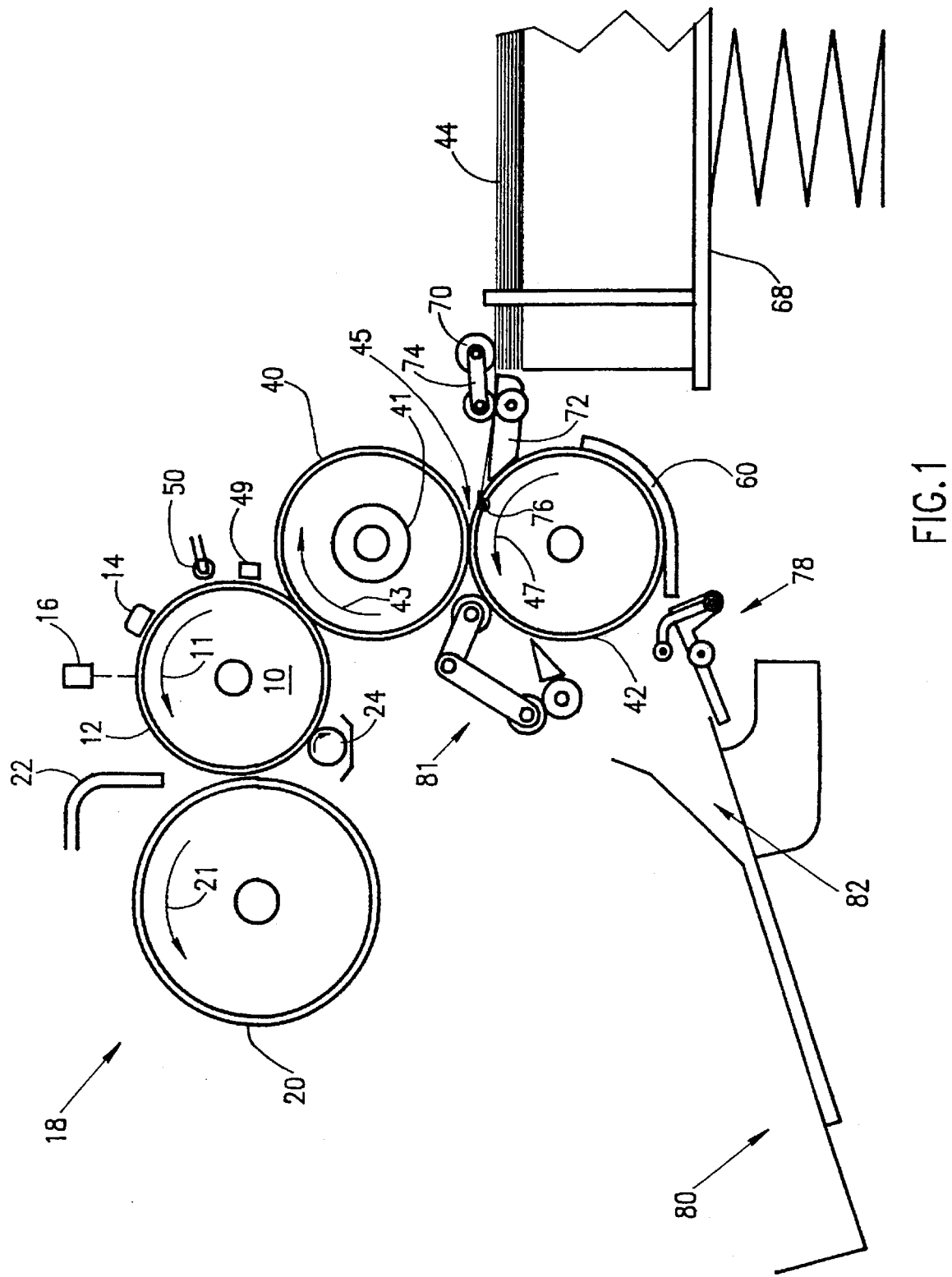
FIG. 1 is a schematic diagram illustrating multi-color imaging apparatus in accordance with a preferred embodiment of the invention.

Reference is now made to FIG. 1 which illustrates a liquid toner multi-color electrographic imaging system in accordance with a preferred embodiment of the present invention.

The apparatus of FIG. 1 includes a drum 10 which rotates in a direction indicated by arrow 11 and which has a photoconductive surface 12 made of selenium or any other photoconductor known in the art. As drum 10 rotates, photoconductive surface 12 passes a charging apparatus 14, such as a corona, which is operative to charge photoconductive surface 12 to a generally uniform predetermined voltage. Further rotation of drum 10 brings charged photoconductive surface 12 past an imager 16, preferably a laser scanner, which is operative to selectively discharge a portion of the charged photoconductive surface by the action of incident light so as to form thereon an electrostatic latent image, the image portions being at a first voltage and the background portions at a second voltage.

Continued rotation of drum 10 brings photoconductive surface 12 bearing the electrostatic latent image into a development region where the latent image is developed by means of a liquid toner developer assembly, referenced generally by numeral 18. Developer assembly 18 includes a developer roller 20, closely spaced from drum 10, and a liquid toner spray apparatus 22. Developer roller 20 typically rotates in the same sense as drum 10, as indicated by arrow 21, such that the surfaces of drum 10 and developer roller 20 have opposite velocities at their region of propinquity. Developer roller 20 is electrified to a voltage that is intermediate the voltages on the background and image portions of the electrostatic latent image on photoconductive surface 12.

Liquid toner spray apparatus 22 supplies liquid toner, containing charged toner particles and carrier liquid, to the area of propinquity between photoconductive surface 12 bearing the latent image and the surface of roller 20. As a result of the relative differences in voltages between the surfaces of roller 20 and the image and background areas of the latent image, toner particles selectively adhere to the image portions of photoconductive surface 12, and the latent image is thereby developed.

In a preferred embodiment of the invention, liquid toner spray apparatus 22 is operative to sequentially provide a multiplicity of pigmented toners, one for each of the process colors, with or without black or other colors, as described in PCT Publication WO 90/14619, the disclosure of which is incorporated herein by reference. Other development apparatus, as known in the art, can also be utilized in imaging apparatus incorporating the duplex printing arrangement of the present invention.

After the latent image has been developed, photoconductive surface 12 is engaged by an excess liquid removal assembly 24, such as a squeegee roller, which serves to compact the toner image, reduce the amount of carrier liquid therein and remove carrier liquid from the background areas on photoconductive surface 12. Squeegee roller 24 is preferably formed of resilient, slightly conductive, polymeric material and is charged to a relatively high voltage with the same polarity as that of the toner particle charge.

Downstream of squeegee roller 24, photoconductive surface 12 bearing the developed image is engaged by intermediate transfer member 40, which may be a drum or belt. Intermediate transfer member 40 preferably has a surface comprising a resilient slightly conductive polymeric material, and which may be heated by means of a heater 41. Alternatively or additionally, intermediate transfer member 40 may be charged to an electric potential having a polarity opposite that of the developed image.

Intermediate transfer member 40 rotates in a direction opposite that of drum 10, as shown by arrow 43, such that there is substantially zero relative motion between their respective surfaces where they contact. As both drum 10 bearing the developed latent image and intermediate transfer member 40 rotate, the developed toner image on photoconductive surface 12 is transferred to the surface of intermediate transfer member 40, by electrophoretic transfer as is well known in the art.

Various types of intermediate transfer members are known and are described, for example in U.S. Pat. No. 4,684,238, PCT Publication WO 90/04216 and U.S. Pat. No. 4,974,027, the disclosures of all of which are incorporated herein by reference.

After the toner image has been transferred from photoconductive surface 12 to intermediate transfer member 40, the photoconductive surface is engaged by a cleaning station 49 which may be any conventional cleaning station as is known in the art. A lamp 50 then removes any residual charge which may remain on the photoconductive surface. Drum 10 then returns to its starting position, ready for recharging and an additional imaging cycle.

After the developed latent image has been transferred from photoconductive surface 12 to intermediate transfer member 40 as described above, it is transferred again in a second transfer procedure from intermediate transfer member 40 to a final substrate 44, such as a sheet of paper. Second transfer, generally aided by heat and pressure, occurs as a result of the engagement of the surface of intermediate transfer member 42 with the substrate at a nip 45 formed with the surface of an impression roller 42. Roller 42 rotates in a direction opposite that of intermediate transfer member 40, as indicated by an arrow 47. In a manner more fully described below, the substrate is fed through nip 45 and the developed image is transferred to the side of the substrate facing intermediate transfer member 40. At the point of transfer, the image is at least partially fused and fixed upon the final substrate as a result of the application of heat and pressure at the nip.

Although a wide variety of toners can be used in the present invention, the preferred toners are those that are suitable for at least partial fixing at the point of transfer, for example, the liquid toner of Example 1 of U.S. Pat. No. 4,842,974. When the preferred liquid toners are used, the temperature and pressure at transfer to the substrate is adjusted so that no additional fusing apparatus is necessary for normal handling of the image.

In an alternative embodiment a powder toner development system is used. In such a system the characteristics of the toner and the velocities, temperatures and pressures of the elements involved are such that, preferably, at least partial fixing of the image to the paper takes place during second transfer.

Simultaneous transfer and fusing of liquid toner images is known and described, for example, in U.S. Pat. No. 4,708, 460, and in PCT Published Application WO 90/4216, the disclosures of which are incorporated herein by reference.

Substrate 44 is initially fed through nip 45 from a spring-mounted tray 68 (located to the right of impression roller 42) which is adapted to hold individual sheets of paper or any other substrate suitable for receiving the developed image. The uppermost sheet in tray 68 is engaged by a roller 70 which, in response to an appropriate control signal, rotates in a clockwise direction and causes the uppermost sheet to move laterally in the direction of nip 45. The sheet is guided towards the nip by means of a fixed plate 72 and one or more pairs of wheels which are attached to plate 72 and to the end of an arm 74 which is pivotally attached to roller 70. A gripper 76, mounted on impression roller 42, is operative to grip the leading edge of the substrate as it is fed to roller 42. The substrate is then conveyed through the nip in the direction of the rotation of roller 42.

After the substrate has been transported through nip 45 and the developed image transferred to the substrate, gripper 76 releases the substrate from engagement with roller 42. In accordance with a preferred embodiment of the invention, the substrate is then directly conveyed, in a manner more fully described below, either to an output tray 80 or to a waiting station 82. For multi-color imaging requiring separate image transfer for each of the process colors, gripper 76 maintains its grip on the substrate as the substrate is repeatedly conveyed around impression roller 42 and through nip 45 until all the color images have been transferred to the substrate. Only then does gripper 76 release substrate 44 for transport either to output tray 80 or waiting station 82.

Figure 2:
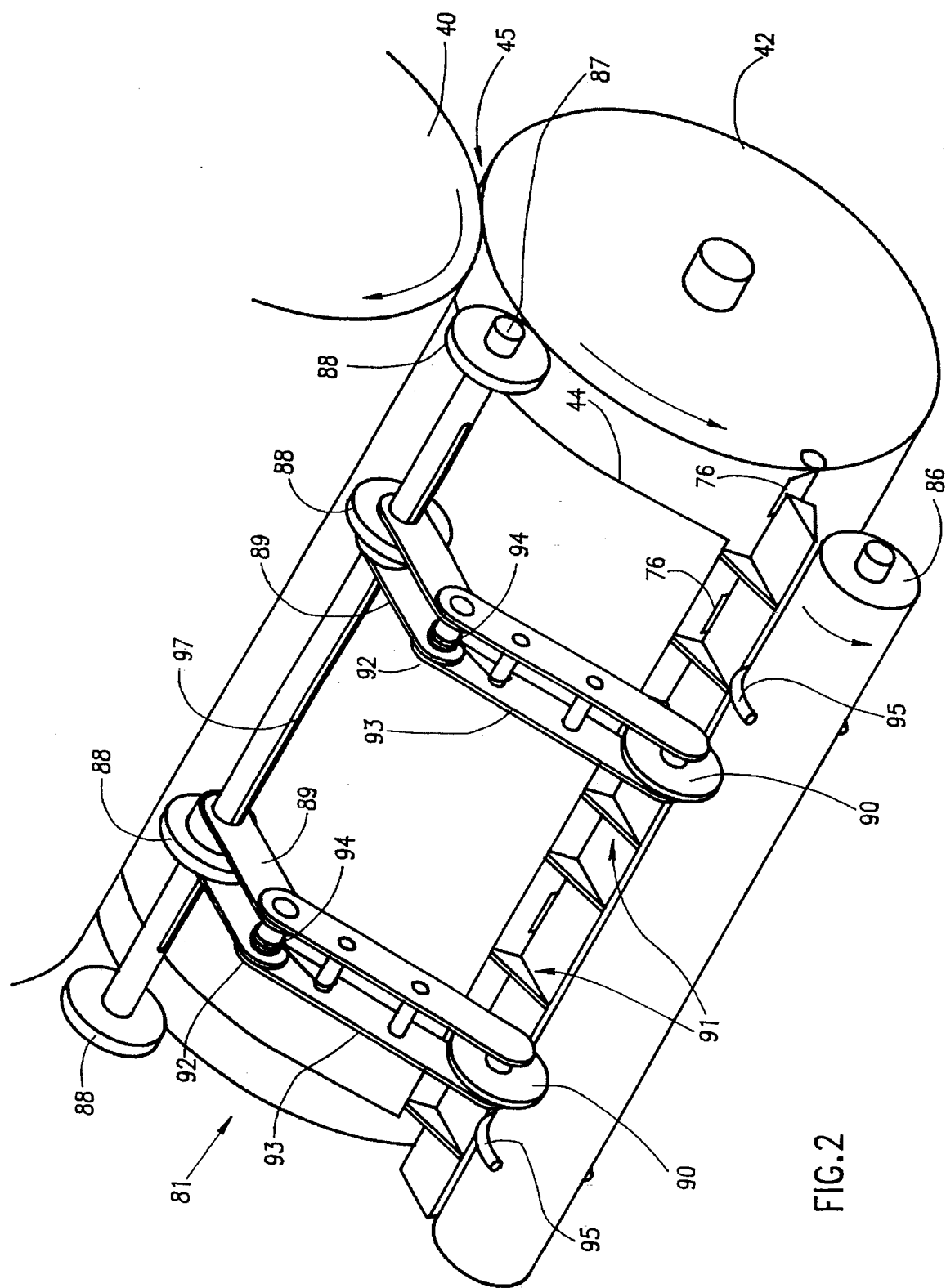
FIG. 2 is a perspective view of substrate deflection apparatus for duplex printing in accordance with a preferred embodiment of the invention.

Reference is now made also to FIG. 2 which shows a perspective view of substrate deflection apparatus 81, in accordance with a preferred embodiment of the present invention. Deflection apparatus 81 includes a shaft 87 which is spaced from impression roller 42 by means of spacers 88 which freely rotate about shaft 87. Fixedly attached to shaft 87 are pairs of arms 89 whose opposite end portions are pivotally attached to pairs of arms 93 at pivots 92. Rotatably attached to the opposite end portions of arms 93 are wheels 90 which engage a motorized roller 86. A spring 94, at pivot 92, is operative to spring load wheels 90 on the surface of roller 86.

Figure 3:
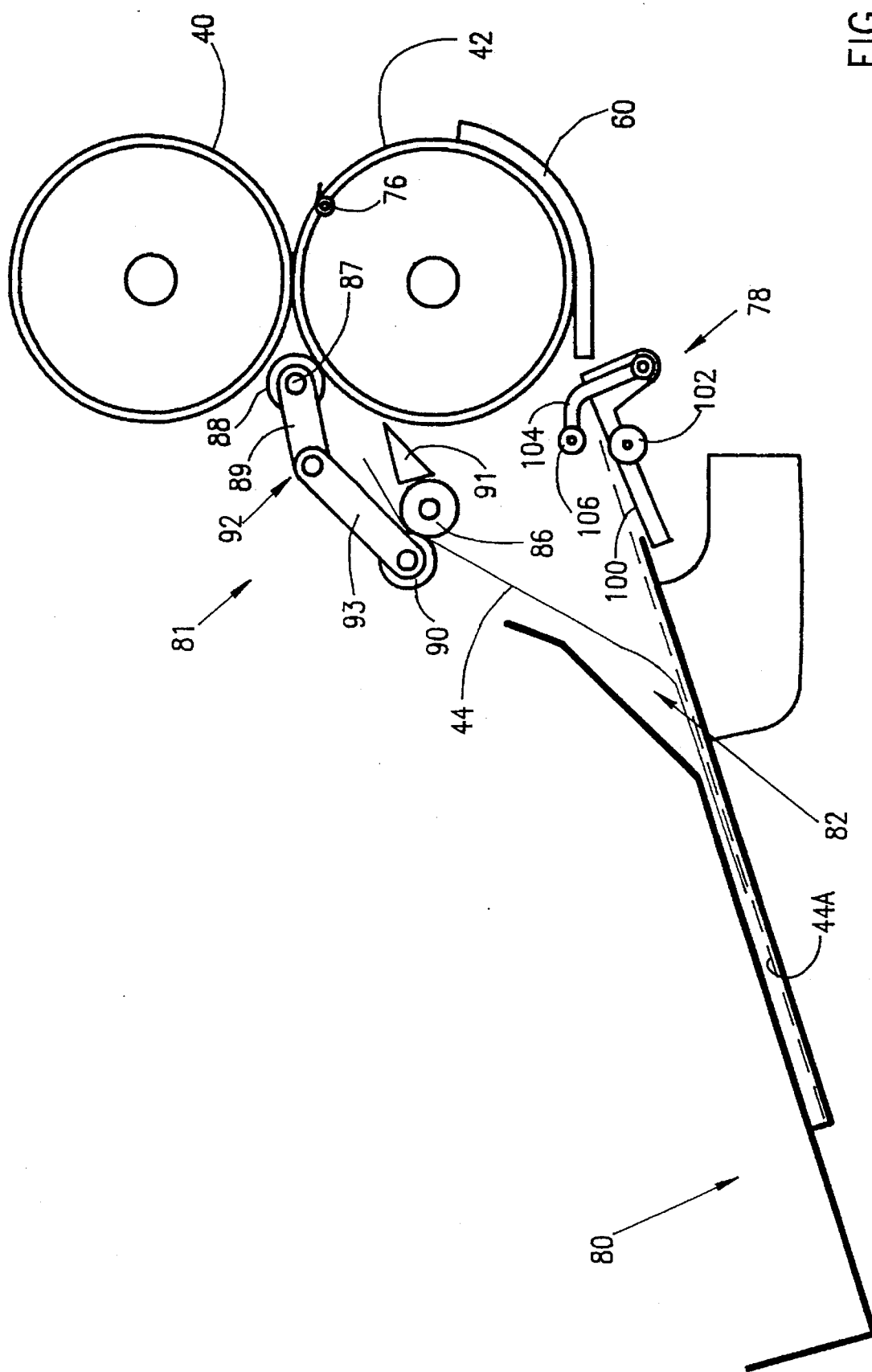
FIG. 3 is a partial side view of the apparatus of FIG. 1 showing operation of the apparatus of FIG. 2 in deflecting a substrate to a waiting station.
Figure 4:
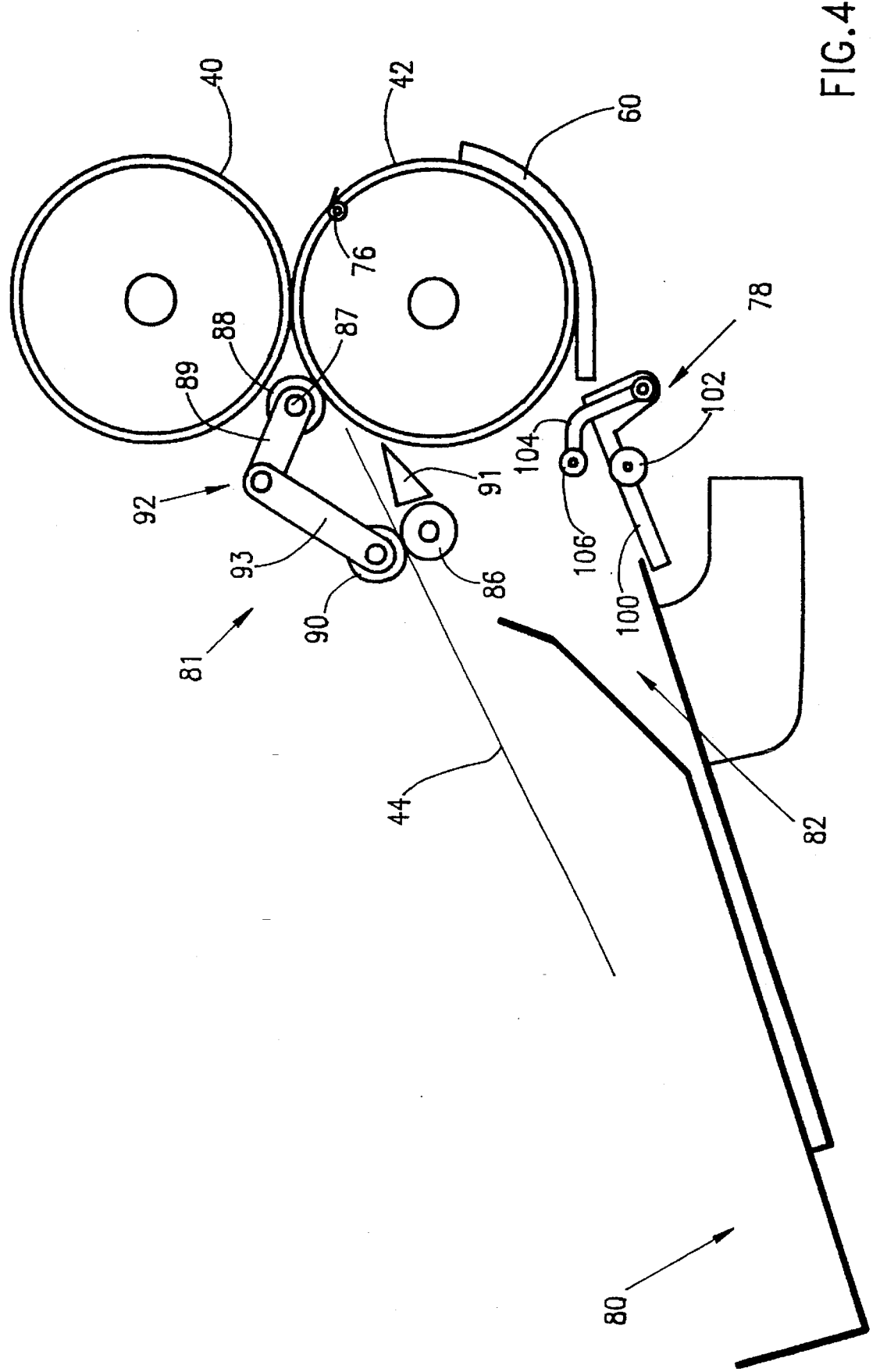
FIG. 4 is another partial side view of the apparatus of FIG. 1 showing operation of the apparatus of FIG. 2 in deflecting a substrate to an output station.

After complete transfer of the toner images to the side of the substrate being printed, gripper 76 opens and releases the substrate at a point just above a stripper 91, as shown in FIG. 2. The substrate is thus directed away from the surface of impression roller 42 and along the face of stripper 91, in the direction of the nip defined by roller 86 and wheels 90. With roller 86 rotating as shown, the substrate is drawn through the nip and is deflected by the action of the nip either to waiting station 82 (as shown in FIG. 3) or to output tray 80 (as shown in FIG. 4). A groove 97 on shaft 87 allows for axial positioning of arms 89 along shaft 87 so as to better accommodate various sizes of substrates.

When it is desired to print an image on the second side of the substrate, the substrate is deflected to waiting station 82, as shown in FIG. 3. In such event, prior to the release of the substrate from gripper 76, shaft 87 is rotated slightly in a counter-clockwise direction, which results in the extension of arms 89 and 93 at pivot 92 such that the effective angle between arms 89 and 93 is close to 180°. This extension of arm 93 results in a displacement of wheels 90 along the surface of roller 86 in a direction away from impression roller 42. When the substrate is drawn through the nip defined by roller 86 and wheels 90, the angle of release is such that substrate 44 is conveyed to waiting station 82, as shown in FIG. 3. The final delivered position of substrate 44 is indicated by reference number 44A. Note that the trailing edge of the substrate lies on wheels 102, whose function is described below in conjunction with FIGS. 5 and 6.

When image transfer to the substrate has been completed (e.g., when printing on both sides of the substrate is complete, or single side printing is desired), the substrate is deflected to output tray 80, as shown in FIG. 4. In such event, prior to the release of the substrate from gripper 76, shaft 87 is rotated slightly in a clock-wise direction, which results in a closing of arms 89 and 93 at pivot 92 such that the effective angle between them is close to 90°. This closing results in an upwards displacement of wheels 90 on the surface of roller 86. When the substrate is drawn through the nip defined by roller 86 and wheels 90, the angle of release is such that substrate 44 is conveyed to output tray 80, as shown in FIG. 4.

A pair of partial rings 95 are situated along roller 86 (but do not rotate with roller 86) as shown in FIG. 2 to provide for a slight bending of the sides of substrate 44 as it engages roller 86, thereby increasing its apparent stiffness and assuring that it is properly deflected to output tray 80. Partial rings 95 are positioned so that they do not engage substrate 44 when the substrate is to be delivered to the waiting station, since the additional stiffening would inhibit the required bending of the substrate as it leaves the nip. Rings 95 are slideable along the surface of roller 86 to accommodate different substrate sizes.

Figure 5:
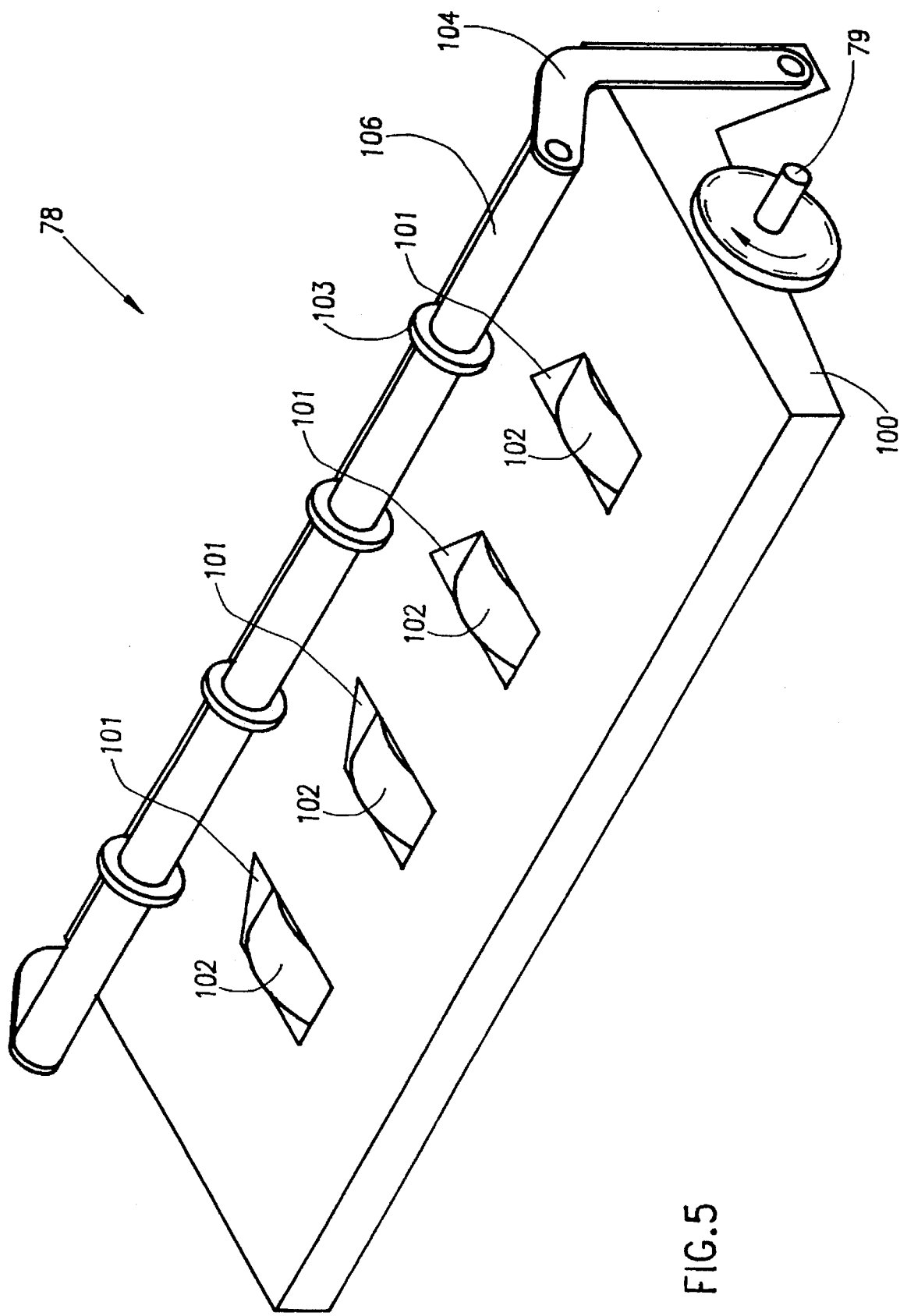
FIG. 5 is a perspective view of substrate transport apparatus for duplex printing in accordance with a preferred embodiment of the invention.

Reference is now made also to FIG. 5 which shows a perspective view of substrate transport apparatus for duplex printing, referenced generally by numeral 78, in accordance with a preferred embodiment of the invention. Transport apparatus 78 preferably includes a set of rubberized wheels 102 which are mounted on a motorized shaft 79 and which protrude through apertures 101 in a plate 100, laterally spaced between impression roller 42 and waiting station 82. Pivotally attached to plate 78 is a curved arm 104, and attached to the opposite end portion of arm 104 is a rod 106. Rod 106 has a set of freely-rotating knurled wheels 103 thereon which are in alignment with wheels 102.

Figure 6:
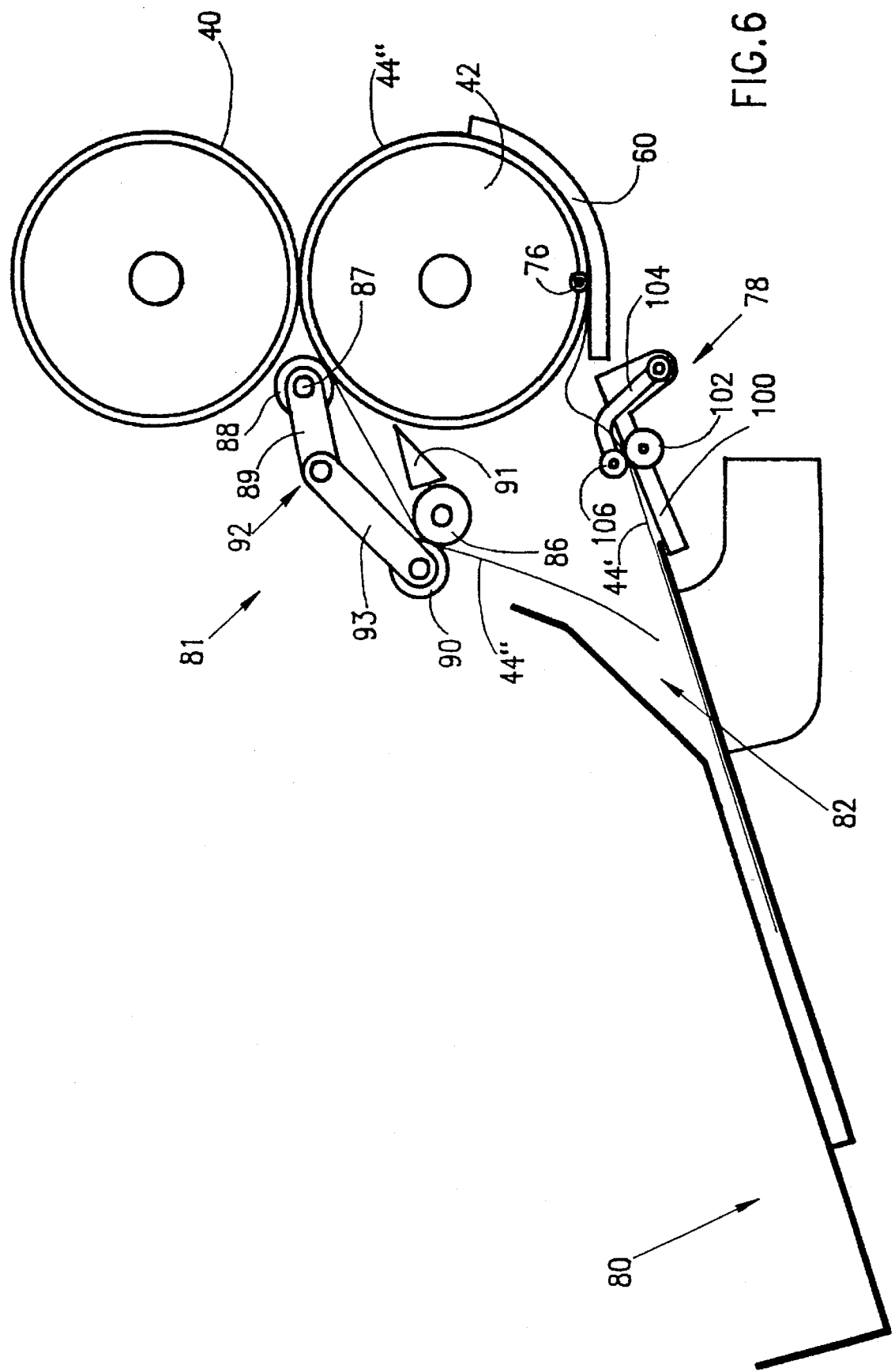
FIG. 6 is a partial side view of the apparatus of FIG. 1 showing operation of the apparatus of FIGS. 2 and 5 with one sheet entering the waiting station while the previous sheet is removed therefrom.

When the substrate is delivered to waiting station 82, arm 104 is in an "upper" open position, as shown in FIGS. 3 and 5, and what was the trailing edge of the substrate falls upon wheels 102. Upon an appropriate signal, arm 104 pivots to a "closed", lower position, as shown in FIG. 6, and the edge of the substrate is then held within a nip defined by wheels 102 and wheels 103. Motorized shaft 79 and wheels 102 then rotate in a clock-wise direction as shown and transport the substrate through the nip to impression roller 42. Alternatively wheels 102 rotate continuously but only move the paper when arm 104 is closed.

The delivery of the substrate to impression roller 42 is timed such that gripper 76 is appropriately located to receive the edge of the substrate as it reaches roller 42. Preferably, the rotation rate of wheels 102 is such that the paper moves faster than the surface of roller 42. This has a twofold advantage. Firstly, the timing of the closing of arm 104 is less critical, since the arm can be closed late allowing the substrate to buckle as shown in FIG. 6. Secondly, the resulting buckle improves the alignment by allowing the edge of the paper to butt against the grippers. To aid the proper placement of the paper in the gripper arms a guide 60 closely spaced from roller 42 is provided.

The substrate is then fed around impression roller 42 and through nip 45. It will be appreciated that in this pass through nip 45, it is the second side of the substrate which faces intermediate transfer member 42, and duplex image transfer is thereby attained. Since the leading edge of the substrate during duplex transfer had been the trailing edge during image transfer to the first side, the image transferred to the duplex side must be inverted in order to maintain the same orientation on both sides of the substrate.

It is a specific feature of some embodiments of the present invention that no more than one substrate is located within waiting station 82 at any one time. As shown in FIG. 6, the apparatus is configured such that a substrate 44' which has been in waiting station 82 is transported back to roller 42 for duplex printing at the same time that another substrate 44" is being delivered to waiting station 82. In this manner, the apparatus is in almost constant operation without any wasted rotations. Thus, the present invention allows for continuous duplex printing without complicated re-feed mechanisms or multi-sheet buffer storage. As a result, in the event of jams or other problems causing an interruption in operation, no more than two sheets need be discarded or reprinted when the system is restarted.

It will also be appreciated that the invention affords the possibility of both single sided and duplex printing, and in the context of duplex printing, several different printing sequences are possible.

In a first preferred embodiment of the invention which maximizes the efficiency of the apparatus, the first side of a first substrate is printed and the substrate is delivered to waiting station 82. Then the first side of a second substrate is printed. While this substrate is being delivered to waiting station 82, the first substrate is removed therefrom and delivered to the impression roller for printing on its second side. While the first substrate is being delivered to the output tray, the second substrate is removed from the waiting station and delivered to the impression roller for printing on its second side. The second substrate is then delivered to the output tray. This process is repeated until all the required prints are completed.

In a second preferred embodiment of the invention which maximizes the efficiency of the apparatus, the first side of a first substrate is printed and the substrate is delivered to waiting station 82. Then the first side of a second substrate is printed. While this substrate is being delivered to waiting station 82, the first substrate is removed therefrom and delivered to the impression roller for printing on its second side. While the first substrate is being delivered to the output tray, the third substrate is delivered to the apparatus for printing on its first side, followed by printing of the second side of the second substrate. This process of alternately printing the second side of a substrate in the waiting station and the first side of a new substrate continues until all the required prints are completed.

It should be understood that the prints on any two succeeding substrates need not be the same. In fact, the duplexer of the present invention is especially suitable for electronic collation in which a number of successive pages are printed with different images to form a set which is then bound by an optional finisher and delivered from the printer. The images to be printed are preferably stored in a fast memory and are successively delivered to the laser imager for forming the successive images on the surface of drum 10.

It will be appreciated by persons skilled in the art that the present invention is not limited to what has been particularly shown and described hereinabove. Rather, the scope of the present invention is defined only by the claims that follow:

We claim:

1. Paper delivery apparatus for a duplex printer comprising:

a shaft;

a motorized roller spaced from the shaft;

at least one pair of arms joined at a pivot and spring loaded with respect to each other at the pivot, one end portion of the pair of arms fixedly attached to the shaft and an opposite end portion having a wheel rotatably attached thereto and defining a nip with respect to the roller;

means for transporting a substrate through the nip;

a waiting station and an output station adapted to receive the substrate upon exiting from the nip; and means for selectably rotating the shaft to first and second positions, such that at the first position the substrate exits from the nip to the waiting station and at the second position the substrate exits from the nip to the output station.

2. Apparatus according to claim 1 wherein rotation of the shaft to the first position causes movement of the wheel along the roller so that the angle of release of the substrate from the nip is such that it is deflected to the waiting station, and rotation of the shaft to the second position causes reverse movement of the wheel along the roller so that the angle of release of the substrate from the nip is such that it is deflected to the output station.

3. Apparatus according to claim 1 wherein the at least one pair of arms comprises at least two pairs of arms axially distance from each other with respect to the shaft.

4. Apparatus according to claim 1 wherein the at the least one pair of arms is axially slideable along the shaft.

5. Apparatus according to claim 4 wherein the at least one roller further includes stiffener members axially slideable thereron.

6. Apparatus according to claim 4 wherein the at least one pair of arms comprises at least two pairs of arms axially distanced from each other with respect to the shaft.

7. Apparatus according to claim 6 wherein the at least two pairs of arms are axially slidable along the shaft.

8. Apparatus according to claim 1 wherein the roller further includes stiffener members axially slidable thereon.

9. Apparatus for printing toner images on both sides of a plurality of sequential substrates comprising:

a printing engine operative to print toner images on one side of a substrate;

a waiting station spaced closely to the printing engine and adapted for holding only one substrate at any one time after printing of images on the first side thereof; and a transport assembly associated with the waiting station which delivers a substrate from the waiting station back to the printing engine for printing on the second side thereof, a first substrate being removed from the waiting station while another substrate is being delivered to the waiting station after printing on the first side thereof, the second side of the first substrate being printed during a printing cycle immediately following printing of the first side of the second substrate.

10. Apparatus according to claim 9 wherein the transport assembly comprises an impression roller which holds a substrate during the printing process, said impression roller being operative to deliver the second substrate to the waiting station after printing one side thereof at the same time as it withdraws the first substrate for printing the second side thereof.

11. Imaging apparatus for duplex printing on a substrate having first and second sides and a leading edge and a trailing edge, the apparatus comprising:

a first member having an image support surface adapted to sequentially support first and second images thereon;

a second member adapted to support the substrate such that one side of the substrate engages the image support surface, leading edge first, at a transfer region;

means for transferring the first image from the image support surface to the first side of the substrate at the transfer region while at least partially fixing the image thereto;

a waiting station adjacent the second member for receiving the substrate after transfer of the first image thereto and prior to the transfer of the second image thereto;

an output station for receiving the substrate after completion of image transfer thereto; and a deflector adjacent the second member which receives the substrate directly from the second member and selectably deflects the substrate towards the waiting station or the output station for delivery thereto;

wherein the deflector comprises a roller and a set of wheels engaging the roller and forming a nip through which the substrate is transported, the set of wheels adapted to engage the roller at first and second positions, at the first position the angle of release of the substrate from the nip is such that it is deflected to the waiting station, and at the second position the angle of release of the substrate from the nip is such that it is deflected to the output station.

12. Apparatus according to claim 11 and including:

a roller assembly associated with the waiting station for selectably engaging the trailing edge of the substrate after the substrate has been delivered to the waiting station and for delivering the substrate back to the second member, the second member being operative to deliver the substrate to the transfer region, whereat the second image is transferred to the second side of the substrate.

13. Imaging apparatus for duplex printing on a substrate having first and second sides and a leading edge and a trailing edge, the apparatus comprising:

a first member having an image support surface adapted to sequentially support first and second images thereon;

a second member adapted to support the substrate such that one side of the substrate engages the image support surface, leading edge first, at a transfer region;

means for transferring the first image from the image support surface to the first side of the substrate at the transfer region while at least partially fixing the image thereto;

a waiting station adjacent the second member for receiving the substrate after transfer of the first image thereto and prior to the transfer of the second image thereto;

an output station for receiving the substrate after completion of image transfer thereto; and a deflector adjacent the second member which receives the substrate directly from the second member and selectably deflects the substrate towards the waiting station or the output station for delivery thereto;

wherein the deflector comprises:
 a shaft;
 a motorized roller;
 at least one pair of arms joined to each other at a pivot and spring-loaded with respect to each other at the pivot, one of the arms fixedly attached to the shaft and the other arm having a wheel rotatably attached thereto and forming a nip with respect to the roller; and
 means for rotating the shaft to a first position at which the deflector deflects the substrate to the waiting station and at a second position at which the deflector deflects the substrate to the output station.

14. Apparatus according to claim 13 and including:

a roller assembly associated with the waiting station for selectably engaging the trailing edge of the substrate after the substrate has been delivered to the waiting station and for delivering the substrate back to the second member, the second member being operative to deliver the substrate to the transfer region, whereat the second image is transferred to the second side of the substrate.

15. Imaging apparatus for duplex printing on a substrate having first and second sides and a leading edge and a trailing edge, the apparatus comprising:

a first member having an image support surface adapted to sequentially support first and second images thereon;

a second member adapted to support the substrate such that one side of the substrate engages the image support surface, leading edge first, at a transfer region;

means for transferring the first image from the image support surface to the first side of the substrate at the transfer region while at least partially fixing the image thereto;

a waiting station adjacent the second member for receiving the substrate after transfer of the first image thereto and prior to the transfer of the second image thereto;

an output station for receiving the substrate after completion of image transfer thereto;

a deflector adjacent the second member which receives the substrate directly from the second member and selectably deflects the substrate towards the waiting station or the output station for delivery thereto; and a roller assembly associated with the waiting station for selectably engaging the trailing edge of the substrate after the substrate has been delivered to the waiting station and for delivering the substrate back to the second member, the second member being operative to deliver the substrate to the transfer region, whereat the second image is transferred to the second side of the substrate;

wherein the roller assembly comprises:
 a base plate having at least one aperture therethrough;
 a motorized rotatable shaft having at least one rubberized wheel mounted thereon and extending through the aperture; and
 at least one roller pivotably mounted with respect to the plate, and selectably operative to form a nip with respect to the at least one wheel for delivery of a substrate therethrough, the at least one roller being in a first disengaged position with respect to the at least one wheel prior to the deflection of a substrate to the waiting station and in a closed, engaged position with respect to the at least one wheel when the substrate is delivered back to the second member.

16. Apparatus according to claim 15 wherein the second member further comprises a gripper which grips the edge of the substrate which enters the transfer region first.

17. Apparatus according to claim 15 wherein the second member is adapted for repeatedly engaging the same side of the substrate with the image support surface, such that at each engagement a different color image is transferred thereto.

18. Apparatus according to claim 15 wherein the deflector comprises a second roller and a set of wheels engaging the second roller and forming a nip through which the substrate is transported, the set of wheels adapted to engage the second roller at first and second positions, at the first position the angle of release of the substrate from the nip is such that the substrate is deflected to the waiting station, and at the second position the angle of release of the substrate from the nip is such that the substrate is deflected to the output station.

19. Apparatus according to claim 15 wherein the deflector comprises:

a shaft;

a motorized roller;

at least one pair of arms joined to each other at a pivot and spring-loaded with respect to each other at the pivot, one of the arms fixedly attached to the shaft and the other arm having a wheel rotatably attached thereto and forming a nip with respect to the motorized roller; and means for rotating the shaft to a first position at which the deflector deflects the substrate to the waiting station and at a second position at which the deflector deflects the substrate to the output station.

20. Apparatus according to claim 15 the deflector is operative to deflect a substrate to the waiting station while the roller assembly is operative to deliver a different substrate from the waiting station back to the second member.

21. Apparatus according to claim 15 wherein the at least one rubberized wheel comprises a motorized set of wheels and the at least one roller is selectably adapted to engage the trailing edge of the substrate at a nip formed with the set of wheels.

22. Apparatus according to claim 21 wherein the at least one roller is adapted to be in an open, disengaged position with respect to the wheels prior to the deflection of a substrate to the waiting station, such that the trailing edge of the substrate contacts the set of wheels when it is deflected to the waiting station, and in a closed, engaged position with respect to the wheels when the substrate is delivered back to the second member.

23. Apparatus according to claim 15 and including means for causing engagement of the first sides of sequential substrates with the image bearing surface for image transfer thereto prior to causing engagement of the second sides of sequential substrates for images transfer thereto.

24. Apparatus according to claim 15 wherein the images are toner images.

25. Apparatus according to claim 15 and including means for printing different images on the first and second substrates.

26. A method for printing images on first and second sides of sequential substrates utilizing apparatus having an image bearing surface and an image transfer region at which images are transferred from the image bearing surface to a substrate during a continuously running cyclic printing sequence comprising:

(a) passing a first substrate through the image transfer region during a first series of printing sequences to print an image on the first side of a first substrate;

(b) delivering the first substrate to a waiting station;

(c) passing a second substrate through the image transfer region during a subsequent series of printing sequences to print an image on the first side of the second substrate;

(d) delivering the second substrate to the waiting station while removing the first substrate therefrom; and (e) passing the first substrate through the image transfer region during the next printing sequence following the subsequent series of printing sequences to print an image on the second side of the first substrate.

27. A method according to claim 26 wherein the subsequent series of printing sequences follows the first series of printing sequences without any intervening printing sequences.

28. A method according to claim 27 wherein the images are toner images.

29. A method according to claim 28 wherein the toner images are liquid toner images.

30. A method according to claim 27 wherein different images are printed on the first and second substrates.

31. A method according to claim 27 and including:

first forming an image on an image forming surface; and transferring the image from the image forming surface to the image bearing surface prior to image transfer to the substrate.

32. A method according to claim 27 wherein the first series of printing sequences comprises a plurality of such printing sequences during each of which overlying images in different colors are printed.

33. A method according to claim 27 wherein the subsequent series of printing sequences comprises a plurality of such printing sequences during each of which overlying images in different colors are printed.

34. A method according to claim 26 wherein the first series of printing sequences comprises a single sequence.

35. A method according to claim 26 wherein the subsequent series of printing sequences comprises a single sequence.

36. A method according to claim 26 wherein the first series of printing sequences comprises a plurality of such printing sequences during each of which overlying images in different colors are printed.

37. A method according to claim 26 wherein the subsequent series of printing sequences comprises a plurality of such printing sequences during each of which overlying images in different colors are printed.

38. A method according to claim 26 wherein passing the substrate through the image transfer region comprises passing the substrate through a nip formed by the image bearing surface in the form of a rotating first cylinder and a second impression cylinder, said nip forming the image transfer region.

39. A method according to claim 26 and comprising:

(f) delivering the first substrate to an output station while removing the second substrate from the waiting station;

(g) printing an image on the second side of the second substrate; and (h) repeating (a)–(g) above for a plurality of sequential substrates.

40. A method according to claim 26 and comprising:

(f) delivering the first substrate to an output station after printing the second side thereof, without first delivering it to the waiting station;

(g) printing an image on the first side of a third substrate;

(h) delivering the third substrate to the waiting station while removing the second substrate from the waiting station;

(i) printing an image on the second side of the second substrate;

(j) repeating (g)–(i) for a plurality of sequential substrates.

41. A method according to claim 26 wherein the images are toner images.

42. A method according to claim 41 wherein the toner images are liquid toner images.

43. A method according to claim 26 wherein different images are printed on the first and second substrates.

44. A method according to claim 26 and including:

first forming an image on an image forming surface; and
transferring the image from the image forming surface to the image bearing surface prior to image transfer to the substrate.

* * * * *

UNITED STATES PATENT AND TRADEMARK OFFICE
CERTIFICATE OF CORRECTION

PATENT NO. : 5,552,875
DATED : September 3, 1996
INVENTOR(S) : O. SAGIV et al.

It is certified that error appears in the above-indentified patent and that said Letters Patent is hereby corrected as shown below:

At column 13, line 20 (claim 20, line 1), before "the" insert ---wherein---.

Signed and Sealed this

Twenty-second Day of April, 1997

Attest:

BRUCE LEHMAN

*Commissioner of Patents and Trademarks*

*Attesting Officer*